United States Patent [19]

Rand

[11] Patent Number: 5,136,077

[45] Date of Patent: Aug. 4, 1992

[54] PROCESS FOR THE PREPARATION OF DIARYL CARBONATES

[75] Inventor: Cynthia L. Rand, Sanford, Mich.

[73] Assignee: The Dow Chemical Company, Midland, Mich.

[21] Appl. No.: 746,284

[22] Filed: Aug. 12, 1991

Related U.S. Application Data

[63] Continuation of Ser. No. 451,894, Dec. 18, 1989, abandoned.

[51] Int. Cl.$^5$ .................. C07C 68/02; C07C 69/96
[52] U.S. Cl. .................. 558/274; 558/268; 558/271; 558/272
[58] Field of Search ............. 558/274, 271, 272, 268

[56] References Cited

U.S. PATENT DOCUMENTS

| | | |
|---|---|---|
| 2,362,865 | 11/1944 | Tryon et al. ............. 558/274 |
| 3,234,261 | 2/1966 | Kurkjy et al. ............ 558/274 |
| 3,234,263 | 2/1966 | Kurkjy et al. ............ 558/274 |
| 3,251,873 | 5/1966 | Kurkjy et al. ............ 558/274 |
| 4,012,406 | 3/1977 | Buysch et al. ........... 558/274 |
| 4,171,422 | 10/1979 | Lazarus et al. ........... 528/437 |
| 4,366,102 | 12/1982 | Rauchschwalbe et al. ... 558/274 |
| 4,658,041 | 4/1987 | Renga .................. 549/229 |

FOREIGN PATENT DOCUMENTS 1361228 9/1964 France.

Primary Examiner—Vivian Garner

[57] ABSTRACT

A process employing an organophosphine catalyst for the reaction of aromatic haloformates with aromatic hydroxy compounds for the production of diaryl carbonates with the elimination of anhydrous hydrogen halide. The organophosphine catalysts of the present invention permit the production of the products in very high yield, and the reaction proceeds at high rates.

14 Claims, No Drawings

PROCESS FOR THE PREPARATION OF DIARYL CARBONATES

CROSS-REFERENCE TO RELATED APPLICATION

This is a continuation of application Ser. No. 07/451,894, filed Dec. 18, 1989, now abandoned.

BACKGROUND OF THE INVENTION

1. Field of the Invention

The present invention relates to a process and a catalyst for the production of diaryl carbonates, and more particularly to a process and a homogeneous catalyst for the homogeneous liquid phase reaction of aromatic haloformates with aromatic hydroxy compounds for the production of diaryl carbonates with the elimination of anhydrous hydrogen halide.

2. Description of the Related Art

Prior art methods for the production of diaryl carbonates have used the interfacial route involving a two phase reaction system and various homogeneous catalytic systems. The interfacial route involves the neutralization of the aromatic hydroxy compound with caustic and the subsequent reaction of an aqueous solution of the phenate type salt of the aromatic hydroxy compound with a carbonyl halide usually phosgene. In the case where the desired product is diphenyl carbonate, excess caustic to insure the complete neutralization of phenol results in a loss of about 20 percent of the phosgene. Salt which represents the loss of two chlor/alkali equivalents is produced. As a consequence, the aqueous stream coming from this reaction process requires treatment prior to disposal. Caustic equivalents include the group 1, 2, 11 and 12 hydroxides, oxides, carbonates and phosphates.

The prior art alternatives to the above described interfacial route to diaryl carbonates are various homogeneous catalytic processes. U.S. Pat. No. 2,362,865 discloses the use of metal phenates as catalysts in the reaction of phenol and phosgene to form diphenyl carbonate in a process in which the phenol is in the liquid phase. U.S. Pat. Nos. 3,234,261 and 3,234,263 relate to the formation of diaryl carbonates from various chloroformates by reaction with metal oxides, with the process of the '263 patent employing a tertiary amine base as a catalyst. Related processes are disclosed in French Pat. No. 1,361,228 and U.S. Pat. No. 3,251,873.

U.S. Pat. No. 4,012,406 discloses a process for the preparation of diaryl carbonates by the reaction of aromatic monohydroxy compounds with phosgene with the aid of an aromatic heterocyclic basic nitrogen compound as a catalyst. Such catalysts are effective for the conversion of haloformates and aromatic hydroxy compounds into diaryl carbonates as would be expected since a haloformate is an intermediate in the reaction of an aromatic hydroxy compound and phosgene to form the same product.

A process for the reaction of aromatic hydroxy compounds with carbonyl halides to produce diaryl carbonates which employs a heterogeneous catalyst system is described in U.S. Pat. application Ser. No. 429,954 filed on Oct. 30, 1989, now abandoned, and refiled as U.S. Ser. No. 07/682,400, filed Apr. 5, 1991, by Harley et.al.

The use aromatic heterocyclic basic nitrogen compounds as catalysts for the reaction of an aromatic haloformate with an aromatic hydroxy compound which is carried out in an inert reaction medium is described in U.S. Pat. application Ser. No. 451,893, filed Dec. 18, 1989, now abandoned, and refiled as U.S. Ser. No. 07/739,778, filed Jul. 30, 1991.

U.S. Pat. No. 4,366,102 discloses a process which employs various organic phosphorus compounds as catalysts for the reaction of a phenol and phosgene to form an aromatic chloroformic ester. This patent teaches that numerous advantages are derived from the use of the catalysts described therein. This patent also teaches that it is surprising that the organic phosphorus compounds of the disclosed process catalyze the reaction to form the ester, but do not promote the further condensation to form the diaryl carbonate.

SUMMARY OF THE INVENTION

The diaryl carbonates produced by the present invention may be converted into polycarbonate resins for use as molding resins by application of heat or some other suitable technique.

The general objective of the present invention is to avoid the disadvantages of the prior art methods of production of diaryl carbonates. These include the water and salt disposal problem associated with the interfacial method, and catalyst degradation and regeneration problems associated with various homogeneous catalytic systems. Another objective of the present invention is to employ organic phosphorus catalyst systems with their numerous technical advantages. Surprisingly, contrary to the teachings of the prior art, it has been found that phosphines promote the reaction between aromatic hydroxy compounds and aromatic haloformates to form diaryl carbonates in very high yields. The rates observed in the process of the present invention are much faster than those observed for prior art processes employing heterocyclic nitrogen bases as catalysts.

The process of the present invention for the production of aromatic carbonates comprises contacting an aromatic haloformate with an aromatic hydroxy compound in the presence of a catalytic amount of a catalyst which comprises at least one organophosphine. The process is carried out in an inert reaction medium comprising an inert atmosphere, and, optionally a noninteracting solvent.

DESCRIPTION OF THE PREFERRED EMBODIMENTS

Desirable aromatic hydroxy starting materials are represented by the general formula

where Ar is an aryl or substituted aryl group with one or more fused rings. R independently selected each occurrence is alkyl, aryl, alkenyl, aryloxy, or alkoxy of 1-12 carbon atoms, and n is an integer. A preferred aromati hydroxy starting material is represented by the formula

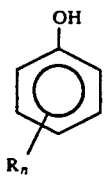

where R independently selected each occurrence is alkyl, aryl, alkenyl, aryloxy, or alkoxy of 1-12 carbon atoms, and n is an integer of 0-5. More highly preferred are phenols wherein R independently selected each occurrence is alkyl, aryl, alkenyl, aryloxy, or alkoxy of 1-6 carbon atoms and n is an integer of 0-3. Other desirable aromatic hydroxy starting materials age bisphenols and naphthols. Highly preferred aromatic hydroxy starting materials are phenol and Bisphenols A and F.

Suitable aryl haloformates of the formula $R_n$—[Ar-]—O—C(O)—X include those in which R—[Ar-]—O—is selected from the same group as $R_n$—[Ar-]—O— of the aromatic monohydroxy compound as discussed above. The $R_n$-[Ar]—O— group of the haloformate may be the same or different from that of the monohydroxy compound. X is a halogen, and a preferred halogen is chlorine.

In a preferred embodiment the aromatic monohydroxy compound is phenol, the aromatic haloformate is phenyl chloroformate and the products of the reaction are diphenyl carbonate (DFC) and anhydrous hydrogen chloride.

Catalysts for the process of the present invention comprise at least one organophosphine, desirably comprising alkyl and aryl phosphines. Preferred phosphines are triphenylphosphine and tributylphosphine, with triphenylphosphine being especially preferred. A catalytic amount of the catalyst may be dissolved, dispersed or supported in the reaction medium.

In one embodiment of the present invention the catalyst is simply dispersed in the reaction medium. If the reaction medium includes a noninteracting solvent, it is desirable that the phosphine catalyst dissolve in the solvent.

In one embodiment where the catalyst is a triaryl phosphine, the aryl groups may be substituted with noninterfering inert groups which preferably are electron donating groups. Examples of suitable groups which may be attached to the aryl groups of the catalyst are alkoxy and alkyl, especially methoxy and methyl.

In another embodiment the catalyst is supported on an inert support such as a polymer, desirably a macroporous styrene-divinylbenzene copolymer resin. The rate of reaction may be decreased when the catalyst is used in this form. However, catalyst manipulations including recycle, may be greatly simplified.

The concentration of catalyst which provides a catalytic amount of the catalyst in the reaction system of the process of the present invention can range from about 0.1 percent to about 10 percent on a mole percent basis based on the reactants. A preferred range for the concentration of the catalyst is from about 0.5 mole percent to about 5 mole percent, with the most preferred range being from about 2 mole percent to about g mole percent.

The process of the present invention desirably is carried out in an inert reaction medium which comprises an inert atmosphere, preferably nitrogen. The reaction may be run with or without a noninteracting solvent. In one embodiment solvents are used which dissolve the catalyst. Suitable solvents include aromatic hydrocarbons, which may be halogenated, of from 6 to 16 carbon atoms. Examples of desirable solvents include xylene, toluene, ethylbenzene, cumene, diisopropylbenzene, chlorobenzene and dichlorobenzene. Other desirable solvents include aliphatic halogenated hydrocarbons such as trichloroethylene, methylene chloride and tetrachloroethylene. A preferred solvent is 1,2-dichlorobenzene (ODCB). A mixture of two or more solvents may be used.

In another embodiment the aromatic haloformate serves as the reaction medium as well as being a reactant.

The process of the present invention may be carried out at temperatures up to the temperature at which the catalyst becomes unstable and decomposes. The desired temperature range is from about 80° C. to about 250° C., with the preferred temperature range being from about 150° C. to about 200° C.

The mole ratio of the reactants can vary. However, a preferred ratio of aromatic haloformate to aromatic hydroxy compound is from about 0.9:1 to about 1:1.5.

The hydrogen chloride produced in the reaction can be removed continuously or intermittently, as desired, and as necessary to relieve the pressure buildup due to the production of this gaseous product.

The following examples and comparative examples are provided to illustrate the process of the present invention, and are not intended to limit the scope of the present invention in any way.

EXAMPLE 1

A series of experiments were run under a standard set of conditions which utilized the following ratio of solvent reactants and catalyst: 1,2-dichlorobenzene (15 mL), phenol (22 mmol, 2.1612 g), phenyl chloroformate (11 mmol. 1.8037 g) and three mol percent of triphenyl phosphine catalyst based on the total number of phenyl groups (33 mmol. 0.1257 g). The phenol and phenyl chloroformate were weighed into a vial, diluted with 15 mL of 1,2-dichlorobenzene (ODCB) and added through a septum to a five necked 25 mL nitrogen purged round bottomed flask. When the reaction temperature was constant at 150°-152° C., the catalyst, dissolved in 3 mL of ODCB, was added to the hot solution. Very rapid evolution of HCl was immediately evident. The extent of reaction was measured by titration of the evolved HCl with respect to time. The amount of HCl evolved over time is equal to the amount of diphenyl carbonate (DFC) formed. The final yields of DFC were verified by liquid chromatography (LC) analysis versus a standard.

The reaction was nearly complete in approximately 24 minutes as analyzed by both titration and LC analysis (84 percent DPC by titration, 87 percent by LC). These results using triphenyl phosphine as a catalyst are fag superior to experiments under identical conditions in which the catalyst is a phosphite, a phosphine oxide or a phosphonium salt. Under comparable experimental conditions triphenylarsine and triphenylamine do not show catalytic activity.

EXAMPLE 2

In the manner described above, phenyl chloroformate (1.8039 g) and phenol (2.1294 g) were reacted using tributylphosphine (0.2096 g) as the catalyst at 150°

C. The evolution of HCl was rapid and after 42 minutes 72 percent DFC had formed.

EXAMPLE 3

Phenyl chloroformate (1.8770 g) and phenol (2.1637 g) were reacted using tris(4-dimethylaminophenyl)-phosphine (0.3947 g) as the catalyst in 15 mL ODCB. After 54 minutes DFC was obtained in 23 percent yield.

EXAMPLE 4

Phenyl chloroformate (1.8031 g) and phenol (2.1228 g) were reacted in 15 mL ODCB at 152° C. using as a catalyst polymer-bound triphenylphosphine supported on styrene-divinylbenzene copolymer (20 percent crosslinked, 0.48 meq/g, 2.125 g). After 38 minutes only 42 percent DFC was observed. The rate of reaction using polymer supported triphenylphosphine was about one seventh of that observed for triphenylphosphine itself.

EXAMPLE 5

The beads from example 4 were filtered in air from the cooled reaction mixture. After washing with methylene chloride (two 10 mL portions) the beads were used as the catalyst for the reaction at 52° C. of phenyl chloroformate (1.8330 g) and phenol (2.1411 g) as above. After 43 minutes 12 percent DFC was observed.

What is claimed is:

1. A process for the production of a diaryl carbonate comprising contacting an aromatic haloformate with an aromatic hydroxy compound selected from the group consisting of phenol, alkyl phenols, alkoxy phenols, halogenated phenol, bisphenol A, bisphenol F and anphthol at a temperature from about 80° to about 250° C. in an inert atmosphere in the presence of a catalytic amount of a catalyst comprising an organophosphine.

2. The process of claim 1 wherein the organophosphine catalyst is an alkyl phosphine or an aryl phosphine.

3. The process of claim 2 wherein the organophosphine catalyst is polymer-bound.

4. The process of claim 2 wherein the organophosphine catalyst is triphenylphosphine or tributylphosphine.

5. The process of claim 1 wherein the aromatic haloformate is phenyl chloroformate and the aromatic hydroxy compound is phenol.

6. The process of claim 1 conducted in the presence of a noninteracting solvent.

7. The process of claim 6 wherein the noninteracting solvent comprises xylene, cumene, toluene, ethylbenzene, diisopropylbenzene, chlorobenzene, dichlorobenzene, trichloroethylene, methylene chloride, tetrachloroethylene, or a mixture of two or more thereof.

8. The process of claim 7 wherein the noninteracting solvent comprises 1,2-dichlorobenzene.

9. The process of claim 1 wherein the concentration of the catalyst is from about 0.1 percent to about 10 percent on a mole percent basis based on the number of moles of the reactants.

10. The process of claim 9 wherein the concentration of the catalyst is from about 0.5 mole percent to about 5 mole percent.

11. The process of claim 10 wherein the concentration of the catalyst is from about 2 mole percent to about 4 mole percent.

12. The process of claim 1 wherein said process is carried out at a temperature from about 150° C. to about 200° C.

13. The process of claim 1, wherein the mole ratio of aromatic haloformate to the aromatic hydroxy compound is from about 0.9:1 to about 1:1.5.

14. The process of claim 1 wherein the aromatic haloformate is the reaction medium for the process.

* * * * *